United States Patent [19]

Nishioka et al.

[11] Patent Number: 4,580,552

[45] Date of Patent: Apr. 8, 1986

[54] ILLUMINATING OPTICAL SYSTEM FOR ENDOSCOPES

[75] Inventors: Kimihiko Nishioka; Nobuo Yamashita, both of Hachiouji, Japan

[73] Assignee: Olympus Optical Co., Ltd., Tokyo, Japan

[21] Appl. No.: 712,472

[22] Filed: Mar. 18, 1985

Related U.S. Application Data

[63] Continuation of Ser. No. 442,669, Nov. 18, 1982, abandoned.

[30] Foreign Application Priority Data

Nov. 19, 1981 [JP] Japan .................... 56-185699

[51] Int. Cl.[4] ............................... A61B 1/06
[52] U.S. Cl. ........................ 128/6; 350/96.26
[58] Field of Search .................. 128/4–8; 350/96.26, 506, 527; 362/32

[56] References Cited

U.S. PATENT DOCUMENTS

| | | | |
|---|---|---|---|
| 4,163,148 | 7/1979 | Fritsche et al. | 350/96.26 |
| 4,217,891 | 8/1980 | Carson | 128/6 |
| 4,350,149 | 9/1982 | Yamashita et al. | 128/6 |

FOREIGN PATENT DOCUMENTS

3028597 2/1981 Fed. Rep. of Germany .......... 128/4

*Primary Examiner*—Edward M. Coven
*Assistant Examiner*—Max F. Hindenburg
*Attorney, Agent, or Firm*—Cushman, Darby & Cushman

[57] ABSTRACT

An endoscope illuminating optical system comprising a light guide in which the distribution of optical fibers on the exit end surface is uneven, a positive lens system placed in front of the exit end of the light guide and a single fiber placed between the positive lens system and exit end to improve the light distribution or to eliminate the uneven illumination produced by the parallax of the illuminating optical system and observing optical system.

4 Claims, 19 Drawing Figures

ILLUMINATING OPTICAL SYSTEM FOR ENDOSCOPES

This is a continuation of application Ser. No. 442,669, filed Nov. 18, 1982, abandoned 3/16/85.

BACKGROUND OF THE INVENTION (a) Field of the Invention:

This invention relates to an endoscope illuminating optical system capable of a wide angle illumination.

Figure 1:
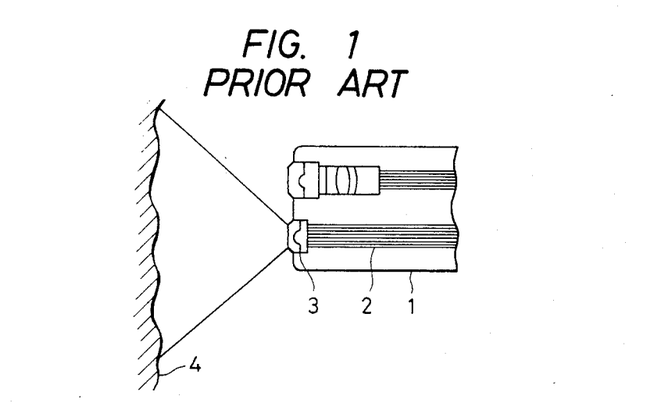
FIGS. 1 and 2 are views respectively showing the first and second conventional endoscope illuminating optical system.
Figure 2:
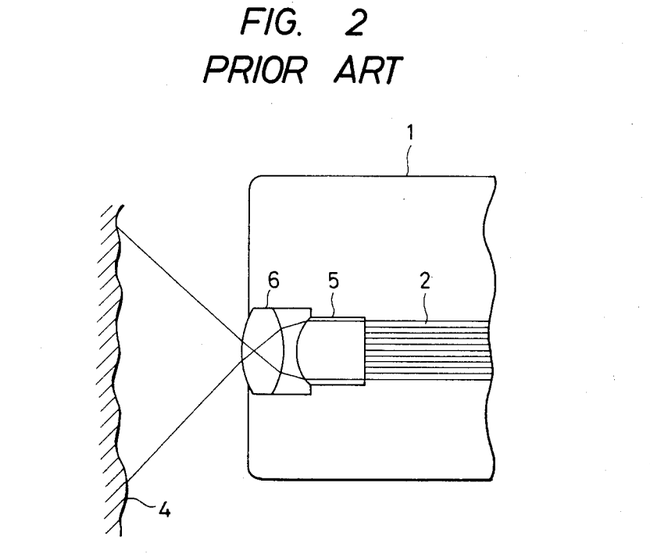
Figure 3:
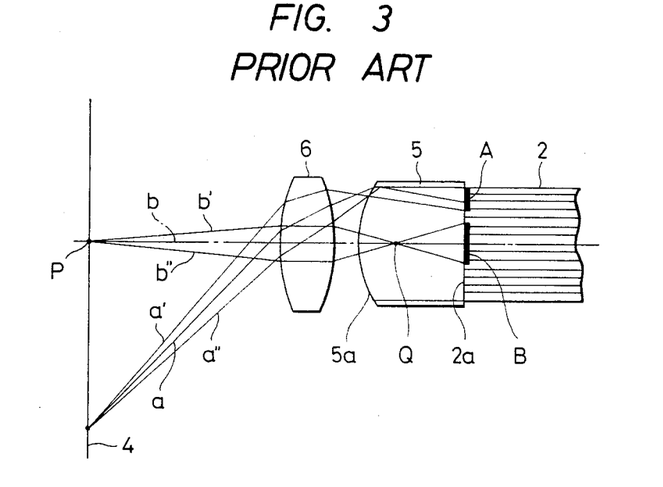
FIG. 3 is a view showing an illuminating state by the second conventional example.
Figure 4:
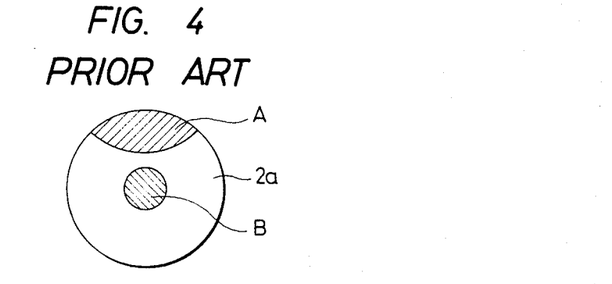
FIG. 4 is a view showing the exit end surface of the light guide of the second conventional example.
Figure 5:
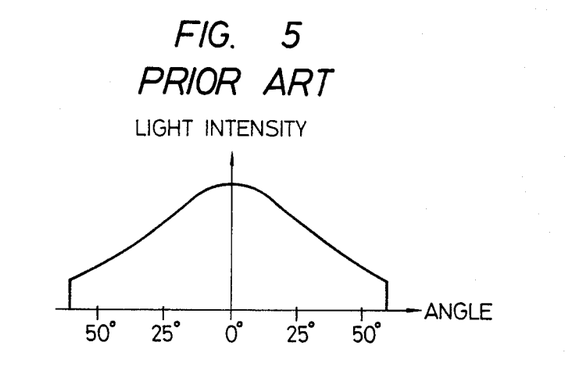
FIG. 5 is a diagram showing the light distribution characteristics of the second conventional example.
Figure 6:
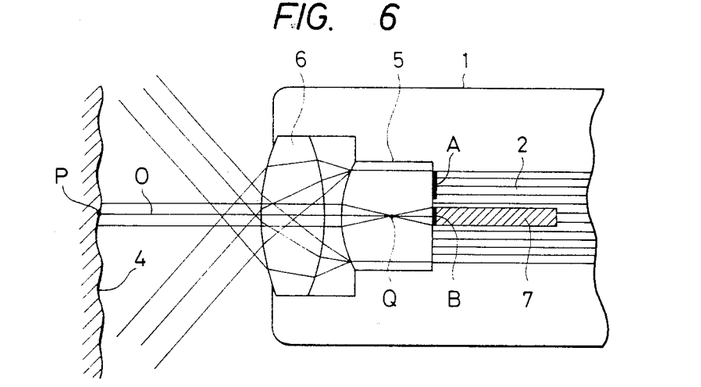
FIG. 6 is a view showing an embodiment of an endoscope illuminating optical system according to the present invention.

(b) Description of the prior art:

The conventional endoscope optical system is formed of a light guide 2 embedded in an endoscope tip part 1 and a concave lens 3 secured to the front end surface of the tip part 1 so as to be positioned near the exit end of the light guide 2 as shown in FIG. 1. However, endoscopes having an observing optical system of a visual angle larger than 100 degrees have recently come to be used to widely observe a surface 4 of such object to be inspected as a body wall. There has been a problem that, with an illuminating optical system, the periphery of a visual field can not be brightly illuminated. Therefore, in order to improve this point, there is conceived such endoscope illuminating optical system as is mentioned, for example, in the Gazette of Japanese Patent Laid Open No. 20428/1981. This is formed of a single fiber 5 cemented to the exit end surface of the light guide 2 and a convex lens 6 secured to the front end surface of the tip part 1 so as to positioned in front of the single fiber as shown in FIG. 2. However, there has been a problem that, even if this illuminating optical system is used, in an endoscope of a visual angle larger than 120 degrees, the periphery of the visual field will be still dark. That is to say, as shown in FIG. 3, the principle of this illuminating optical system can be considered to be that the image of the exit end 5a of the single fiber 5 is projected on the surface 4 of the object to be inspected by the convex lens 6. The lights a, a' and a" illuminating the periphery of the visual field are the lights coming out of the edge of the exit end surface 5a and the lights illuminating the center P of the visual field are the lights coming out of a point Q in the single fiber 5. By the way, the point Q is not on the exit end surface 5a of the single fiber, because the convex lens 6 has a distortion and the exit end surface 5a projects forward. Further, the lights passing through the edge of the exit end surface 5a come also out of the zone A in the peripheral part of the exit end surface 2a of the light guide 2. As shown in FIG. 4, the zone A is of a shape enclosed with two arcs and the lights passing through the point Q come out of the circular zone B in the central part of the exit end surface 2a of the light guide 2. Therefore, as shown in FIG. 5, t;he light distribution characteristics in this case are such that the center of the visual field is bright and the peripheral part is gradually dark. With such light distribution characteristics, the surface 4 of the object to be inspected will be obstructed by the brightness in the center and will not be seen unless it is made brighter to some extent. That is to say, in fact, the part of the surface 4 of the object to be inspected on which the illuminating light little reaches will not be able to be observed. Particularly, in such case as of photographing, if the dark peripheral part is also to be photographed, the bright center part will be photographed to be really white (so bright as to be overexposed). It is not practical. If the center is to be photographed so as to be definitely seen, the peripheral part will be so dark as to be photographed to be really black and the result will be the same as of a narrow illuminated range (narrow visual angle). By the way, the single fiber means a thick optical fiber provided with a core and clad and may be considered to be one made thick of optical fibers used for a light guide or the like.

SUMMARY OF THE INVENTION

In view of the above described circumstances, a primary object of the present invention is to provide an endoscope illuminating optical system wherein a wide angle illumination is possible and no uneven illumination is made.

According to the present invention, this object is attained by being provided with a light guide made of an optical fiber bundle in which the distribution of the optical fibers on the exit end surface is uneven, a positive lens system placed in front of the exit end surface and a tubular reflector placed between the positive lens system and exit end surface.

According to a preferred formation of the present invention, the number of optical fibers forming the optical fiber bundle as a light guide per unit area is larger in the peripheral part than in the central part of the exit end surface and a single fiber is used for the tubular reflector so that the entire surface of the object to be inspected can be uniformly illuminated. In order to make the number of optical fibers per unit area larger in the peripheral part than in the central part, a bar-shaped member made of such material passing no light as a metal, plastic of glass can be embedded in the optical axial direction. The light guide can be made movable in the optical axial direction.

According to another preferred formation of the present invention, the number of optical fibers forming the optical fiber bundle as a light guide per unit area is smaller in only a part of the periphery than in other parts of the exit end surface and a single fiber is used for the tubular reflector so that the light distribution to the surface of the object to be inspected can be adjusted so as to eliminate the uneven illumination produced by the parallax of the illuminating optical system and observing optical system. In order to make the number of optical fibers per unit area smaller in only a part than in other parts of the exit end surface, the above mentioned bar-shaped member can be embedded in the lengthwise direction in the peripheral part of the exit end of the light guide.

The positive lens system comprises one convex lens and the single fiber has a convex surface on the side facing the positive lens system. The positive lens system can further comprise another convex lens cemented to the single fiber.

DESCRIPTION OF THE PREFERRED EMBODIMENTS

First, with reference to FIGS. 6 to 9, the present invention shall be explained by using the same reference numerals as are used in FIGS. 1 to 5 for the members and parts substantially identical with those already described in connection with FIGS. 1 to 5. The reference numeral 7 denotes a bar-shaped member made of such material passing no light as a metal, plastic or glass and embedded in the central part of the exit end of a light guide 2.

Figure 7:
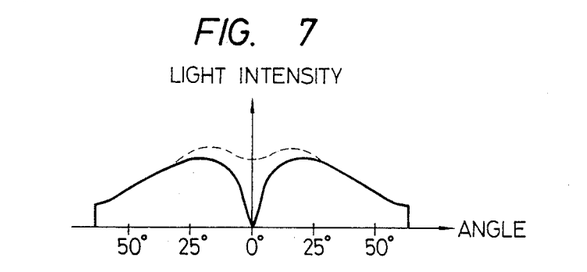
FIG. 7 is a diagram showing the light distribution characteristics of the embodiment in FIG. 6.

As the endoscope illuminating optical system according to the present invention is thus formed, if the bar 7 is to completely cover the zone B, the light distribution characteristics will be as illustrated by the solid line FIG. 7 and no light will come at all to the center of the visual field but, if the bar 7 is not to completely cover the zone B, the light distribution characteristics will be as illustrated by the dotted line in FIG. 7, the brightness of the center and periphery of the visual field will be uniform, therefore the same effect as of an apparent wide angle will be obtained and, even with a wide angle endoscope, even the visual field periphery will be seen. Also, if the bar 7 is embedded in the central part of the exit end of the light guide 2, the exit end surface 2a of the light guide 2 will be equivalent to becoming larger and the illuminated field will become wider, that is to say, the illumination will be the same as being made wider in the angle.

Figure 8:
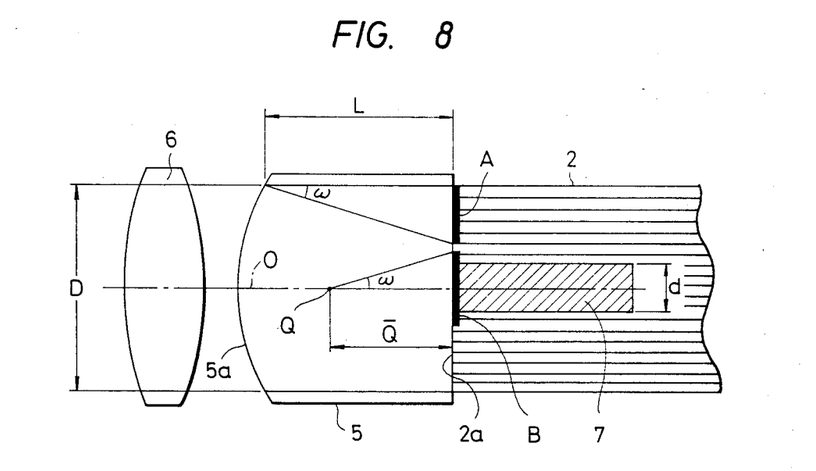
FIGS. 8 and 9 are explanatory views of the conditions of the embodiment in FIG. 6.
Figure 9:
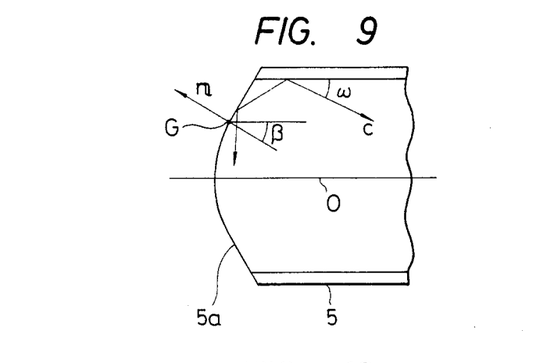

Next, more particularly, the relation among the diameter d of the bar 7, the length L of the single fiber 5 (wherein L shall be the distance from the edge of the exit end surface 5 $a$ of the single fiber 5 to the exit end surface 2a of the light guide 2) and the diameter D of the single fiber 5 shall be described. In FIG. 8, the distance from the point Q to the exit end surface 2a of the light guide 2 shall be represented by $\overline{Q}$ and the maximum angle made by the light in the single fiber 5 with the optical axis O shall be represented by $\omega$. First, if the bar 7 completely enters the zone A, even the light amount of the visual field periphery will decrease. In order to prevent it, $$D - 2L \cdot \tan \omega \geq d \tag{1}$$

will be a required condition. Also, for the condition of preventing the cross sections of the fibers of the light guide 2 from being projected on the surface 4 of the object to be inspected, $$\overline{Q} \cdot \tan \omega \geq \phi \tag{2}$$

is required (wherein $\phi$ represents the diameter of one fiber of the light guide 2), because, as the point P corresponds to the image point of the point Q, if the exit end surface 2a of the light guide 2 is placed at the point Q, the cross sections of the fibers of the light guide 2 will be projected on the surface of the object to be inspected and the surface will be hard to see. Therefore, the exit end surface 2a of the light guide 2 must be separated from the point Q. If $\overline{Q}$ tan $\omega$ which is the size of the unfocused circle is equal to or larger that $\phi$, the cross sections of the fibers of the light guide 2 will not be visible. In fact, there is no fiber but the bar 7 on the optical axis. However, the above mentioned idea applies also to a point on the object surface 4 separate from the optical axis O. Even then, for the condition of preventing the cross sections of the fibers of the light guide 2 from being projected on the point comparatively near to the optical axis O, the formula (2) is required. As shown in FIG. 8, in case the exit end surface 5a of the single fiber 5 is made a curved surface convex toward the convex lens 6, the curved surface shape had better be limited as described below. That is to say, as shown in FIG. 9, if a light c passing through any one point on the exit end surface 5a of the single fiber 5 and making a maximum angle with the optical axis O in the single fiber 5 is considered, the condition of preventing this light c from being totally reflected by the exit end surface 5a of the single fiber 5 will be $$|\beta| \leq \sin^{-1}(1/n) - \omega \tag{3}$$

where n represents the refractive index of the core of the single fiber 5, $\beta$ represents the angle made by the normal vector n of the curved surface with the optical axis O and $\omega$ represents the maximum angle made the light c with the optical axis O. If the curved surface fails to satisfy the condition of the formula (3), the lights will be totally reflected on the exit end surface 5a of the single fiber 5 and the light amount will be lost. In fact, the intensity of the light of a large angle made with the optical axis O is generally so low that the formula (3) may be made such loose condition as in the following:

$$|\beta| \leq 2(\sin^{-1}(1/n) - \omega) \tag{4}$$

Figure 10:
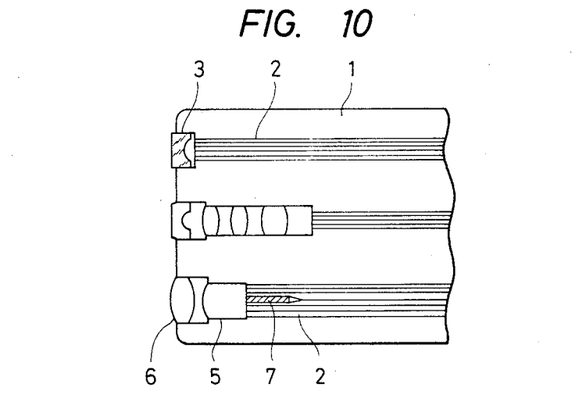
FIGS. 10 and 11 are views respectively showing the second and third embodiments of the present invention.

Now, another embodiment of the present invention shall be explained. FIG. 10 is of the second embodiment wherein the first conventional illuminating optical system shown in FIG. 1 in which the concave lens 3 is placed in front of the light guide 2 and the above mentioned first embodiment are combined with each other. It is prevented by combining the above mentioned first conventional example that, with only the above mentioned first embodiment, depending on the selection of the diameter of the bar 7, no light will come at all to the visual field center as illustrated by the solid line in FIG. 7.

Figure 11:
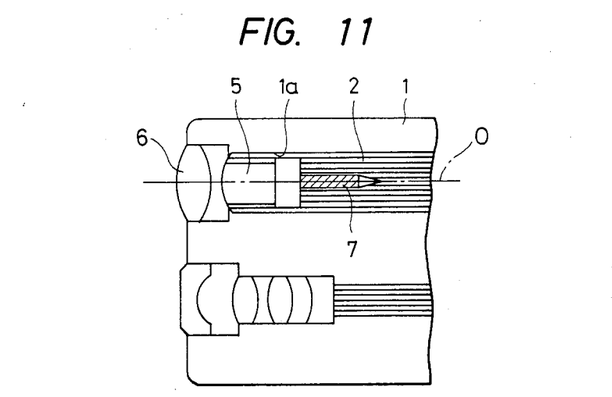

FIG. 11 is of the third embodiment wherein the light guide 2 is arranged so as to be movable in the optical axial direction within the cylindrical chamber 1a in the tip part 1 in the first embodiment. According to this embodiment, as the position of the bar 7 varies, the light distribution can be varied in response to the object. Also, as the inside surface of the cylindrical chamber 1a is exposed to light, the inside surface had better be made a reflecting surface.

Figure 12:
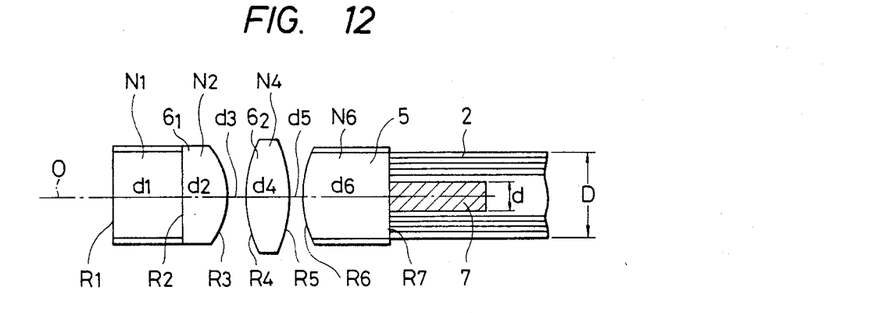
FIG. 12 is a view showing the fourth embodiment of the present invention.
Figure 13:
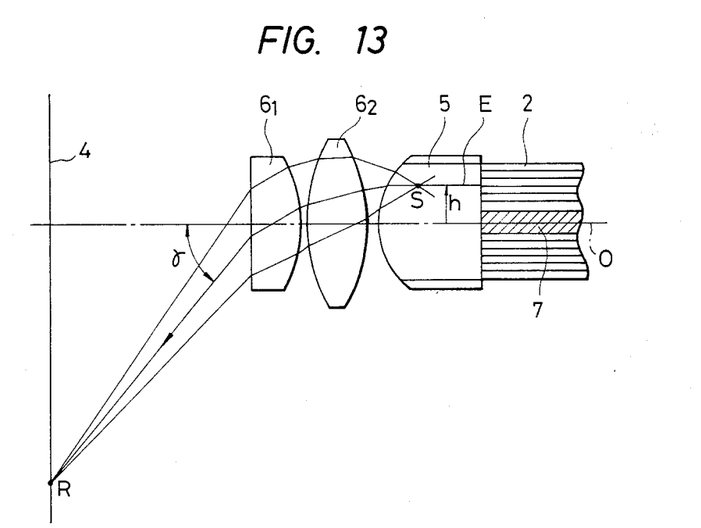
FIG. 13 is an explanatory of the distortion of the fourth embodiment.

FIG. 12 is of the fourth embodiment wherein the convex lens 6 in the case of the above mentioned first embodiment is formed of two convex lenses 6₁ and 6₂ (the round-sectioned bar of the single fiber fitted to the front surface of the convex lens 6₁ is not counted in the number). When the number of the convex lenses of the formation is increased to two from one, the distortion of the convex lenses will be able to be reduced and, as a result, even the periphery of the visual field will be able to be brightly illuminated. The distortion in this case shall be explained more particularly with reference to FIG. 13. One point R outside the optical axis O on the object surface 4 shall be an image point and the point S in the single fiber conjugate with the image point R with respect to the convex lenses 6₁ and 6₂ shall be an object point. As the light bundle coming out of the light guide 2 is rotary symmetrical with the straight line parallel with the optical axis O, the main light E of the object point S can be considered to be a light passing through the object point S and parallel with the optical axis O. If the distortion is considered with respect to the main light E, the exit angle of the main light E will increase so quickly with the increase of the distance h of the main light E from the optical axis O that it will be a positive distortion. Therefore, the light emitted from a unit area of the single fiber conjugate with the object surface 4 with respect to the convex lenses 6₁ and 6₂ will be projected on the wider object surface 4 with the increase of the distance h and therefore the object surface 4 will be darker on the periphery of the visual field. In order to reduce the positive distortion, the number of the convex lens may be increased. Therefore, the number of the convex lenses is made two in this fourth embodiment. By the way, in this embodiment, the round-sectioned bar formed of the single fiber is fitterd to the front surface of the convex lens 6₁, because, with only the convex lens 6₁, it will be difficult to make the waterproofing effect sufficient in the case of fitting it to the tip part of the endoscope. Therefore, the round-sectioned bar is pasted to the front surface of the convex lens 6₁ to increase the length of the peripheral part of the lens. If an ordinary glass plate is used instead of the single fiber, the light will reach the mat part of the side surface of the glass plate and will be lost. This is not desirable. If the single fiber is used, there will be no such thing.

By the way, in the above mentioned respective embodiments, the bar 7 passing no light is embedded in the central part of the exit end of the light guide 2. When the distribution of the optical fibers of the light guide 2 is made coarse in the center but dense on the periphery, the same effect will be able to be obtained. Also, such tubular reflector as of a metal pipe whose inside surface is a reflecting surface or a glass bar ground on the periphery can be used instead of the single fiber 5.

Figure 14:
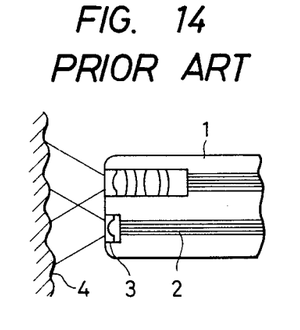
FIGS. 14 and 15 are views respectively showing the illuminating state and endoscope visual field by the first conventional example.
Figure 15:
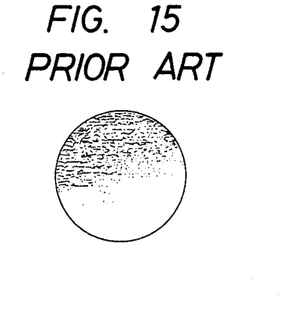
Figure 16:
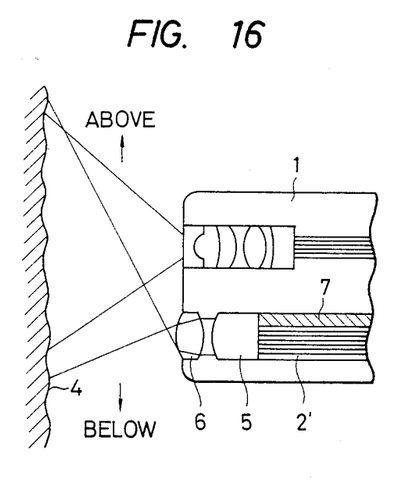
FIG. 16 is a view showing the illuminating state by the fifth embodiment of the present invention.
Figure 17:
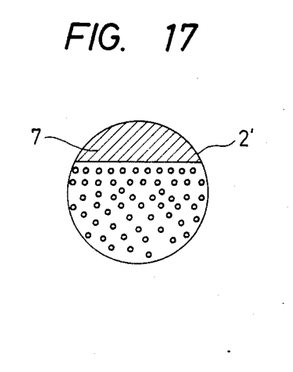
FIGS. 17 and 18 are views respectively showing the cross section of the exit end of the light guide and the light distribution characteristics of the fifth embodiment.
Figures 18, 19:
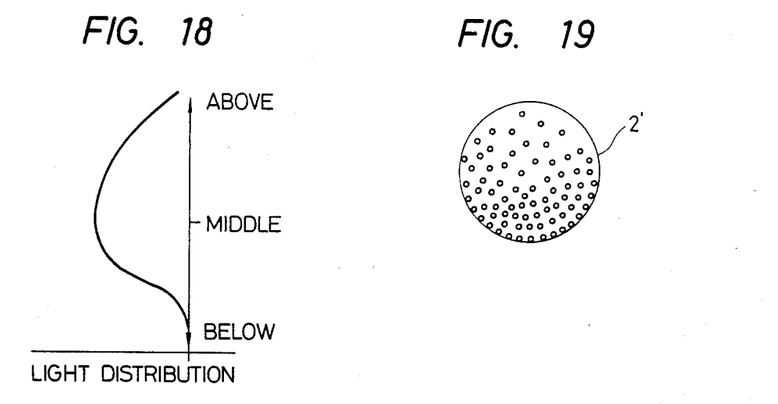
FIGS. 19 is a view showing another example of the cross section of the exit end of the light guide.

According to the illuminating optical system of the present invention, not only the light distribution in the wide angle endoscope can be improved but also the uneven illumination produced by the parallax of the illuminating optical system and observing optical system can be eliminated. This shall be described more particularly. FIG. 14 shows the case of observing the approached object surface 4 in the above mentioned first conventional endoscope illuminating optical system. As the observing optical system and illuminating optical system are arranged at a spacing from each other, such uneven illumination as is dark in the upper part but is bright in the lower part as shown in FIG. 15 will be made. In the fifth embodiment shown in FIG. 16, such uneven illumination is eliminated, a light guide 2' in which a part of the periphery is replaced with the bar 7 is used instead of the light guide 2 in the above mentioned first embodiment and the cross section of the exit end of this light guide 2' is as shown in FIG. 17. Thus, as shown in FIG. 18, the light distribution can be made bright in the upper part of the visual field but dark in the lower part and therefore, as a result, the visual field can be uniformly illuminated. That is to say, by properly removing a part of the light guide from the exit end of the light guide, the light distribution can be adjusted according to the object. By the way, this idea can be used for a means of avoiding the trouble of the case that the light from the light guide reaches the nozzle and hood of the endoscope. Further, even with the light guide 2' in which a part of the periphery is replaced with the bar 7 or the distribution of the optical fibers is not uniform as shown in FIG. 19, the same effect can be obtained.

Examples of numerical values of the illuminating optical system according to the present invention shall be shown in the following by using the fourth embodiment shown in FIG. 12 wherein $d_1$ to $d_6$ represent distances between the respective surfaces and $N_1$ to $N_6$ represent refractive indices of the respective lenses or cores of single fibers.

| | R | d | N |
|---|---|---|---|
| 1 | ∞ | 2.7 | 1.80518 |
| 2 | ∞ | 1.6 | 1.883 |
| 3 | −1.868 | 0.34 | |
| 4 | 3.447 | 1.9 | 1.883 |
| 5 | −58.557 | 0.13 | |
| 6 | 10.823 | 2.4 | 1.62 |
| 7 | ∞ | | |

D = 3.1 mm, d = 0.67 mm, ω = 18°, L = 2.29 mm,
φ = 0.03 mm, $\overline{Q}$ ≈ 2.35 mm, D − 2L tan ω = 1.612 mm,
$\overline{Q}$ tan ω = 0.764 mm, maximum value of β = 8.234°, $$2\left(\sin^{-1}\frac{1}{n} - \omega\right) = 40.236°.$$

By the way, $N_1$ to $N_6$ represent refractive indices of the cores of single fibers and the refractive index of their clad is 1.52.

We claim:
1. An illuminating optical system for endoscopes comprising a light guide having an optical axis and which consists of an optical fiber bundle and a bar-shaped member embedded within said optical fiber bundle and extending along said optical axis of said light guide from the exit end face of said light guide into said light guide to improve the light distribution pattern emitted from the light guide, a positive lens system arranged in front of said exit end face of said light guide and a tubular reflector arranged between said exit end face and said positive lens system.

2. An illuminating optical system for endoscopes according to claim 1 wherein said tubular reflector is any one of a single fiber, a metal pipe whose inside surface is a reflecting surface and a glass bar ground on the peripheral surface and said positive lens system comprises at least one positive lens.

3. An illuminating optical system for endoscopes according to claim 1 wherein said bar-shaped member is arranged so as to be made of any one of metal, plastics and glass.

4. An endoscope comprising an illuminating optical system provided with a light guide having an optical axis and which consists of an optical fiber bundle, a positive lens system arranged of said light guide and a tubular reflector in front of said exit end face arranged between said exit face end and said positive lens system and comprising an observing optical system arranged in parallel with said illuminating optical system wherein the density, on the exit end face of said light guide, of optical fibers to form said optical fiber bundle is lower in the peripheral area of said exit end face than in other areas of said exit end face, and wherein a bar-shaped member extending in parallel with said optical axis of said light guide is embedded in the peripheral area of said light guide and the density of optical fibers in said peripheral area of said light guide is zero.

* * * * *

UNITED STATES PATENT AND TRADEMARK OFFICE
CERTIFICATE OF CORRECTION

PATENT NO. : 4,580,552

DATED : April 8, 1986

INVENTOR(S) : NISHIOKA et al

It is certified that error appears in the above-identified patent and that said Letters Patent is hereby corrected as shown below:

Column 7, line 3, claim 3, delete "arranged so as to be"

Column 7, line 8, claim 4, after "arranged" insert--in front of said exit end face--

Column 7, line 9, claim 4, after "reflector" delete "in front of said exit end face"

Column 7, line 10, claim 4, change "exit face end" to--exit end face--

Signed and Sealed this

Eighteenth Day of November, 1986

*Attest:*

DONALD J. QUIGG

*Attesting Officer*   *Commissioner of Patents and Trademarks*